(12) United States Patent
Takeuchi et al.

(10) Patent No.: US 10,962,450 B2
(45) Date of Patent: Mar. 30, 2021

(54) SPECIMEN COLLECTION DEVICE, HOLDER FOR SPECIMEN COLLECTION DEVICE, AND SPECIMEN PRE-PROCESSING METHOD THAT USES SPECIMEN COLLECTION DEVICE

(71) Applicant: SHIMADZU CORPORATION, Kyoto (JP)

(72) Inventors: Ippei Takeuchi, Kyoto (JP); Yoichi Fujiyama, Kyoto (JP); Shinobu Kudoh, Kyoto (JP); Koji Inoue, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 392 days.

(21) Appl. No.: 16/068,896

(22) PCT Filed: Jun. 6, 2016

(86) PCT No.: PCT/JP2016/066776
§ 371 (c)(1),
(2) Date: Jul. 10, 2018

(87) PCT Pub. No.: WO2017/122372
PCT Pub. Date: Jul. 20, 2017

(65) Prior Publication Data
US 2019/0011334 A1 Jan. 10, 2019

(30) Foreign Application Priority Data
Jan. 14, 2016 (WO) .................. PCT/JP2016/050943

(51) Int. Cl.
*G01N 1/14* (2006.01)
*G01N 1/10* (2006.01)
(Continued)

(52) U.S. Cl.
CPC ................. *G01N 1/14* (2013.01); *A61B 5/15* (2013.01); *A61B 5/150022* (2013.01);
(Continued)

(58) Field of Classification Search
CPC .. G01N 1/14; G01N 1/10; G01N 1/18; G01N 33/48; A61B 5/15
See application file for complete search history.

(56) References Cited

U.S. PATENT DOCUMENTS 3,475,127 A 10/1969 Gilford
9,908,113 B2 3/2018 Sloan et al.
(Continued)

FOREIGN PATENT DOCUMENTS

CN 105209880 12/2015
EP 0742735 11/1996
(Continued)

OTHER PUBLICATIONS

"International Search Report (Form PCT/ISA/210)" of PCT/JP2016/066776, dated Aug. 16, 2016, with English translation thereof, pp. 1-5..
(Continued)

*Primary Examiner* — Brian J. Sines
(74) *Attorney, Agent, or Firm* — JCIPRNET

(57) ABSTRACT

This specimen collection device has a channel through which a specimen can be drawn by capillarity. The channel has two channel sections that extend from the tip side to the base side and are connected at the tip side. One of the channel sections is connected to a base side specimen intake port, and the other terminates at a location prior to reaching the base end. An air hole is provided at this terminating location. The specimen collection device is equipped with an extraction unit for collecting a prescribed amount of the specimen. The extraction unit includes the two channel
(Continued)

sections on the tip side of the air hole, and can be severed from the other sections of the device body of the specimen collection device via a severable section.

18 Claims, 11 Drawing Sheets

(51) Int. Cl.
*G01N 1/18* (2006.01)
*G01N 33/48* (2006.01)
*A61B 5/15* (2006.01)
*G01N 1/12* (2006.01)
*B01L 3/00* (2006.01)
*B01L 9/00* (2006.01)

(52) U.S. Cl.
CPC .. *A61B 5/150213* (2013.01); *A61B 5/150251* (2013.01); *A61B 5/150343* (2013.01); *A61B 5/150755* (2013.01); *B01L 3/5021* (2013.01); *B01L 9/527* (2013.01); *G01N 1/10* (2013.01); *G01N 1/12* (2013.01); *G01N 1/18* (2013.01); *G01N 33/48* (2013.01); *B01L 3/502723* (2013.01); *B01L 2200/027* (2013.01); *B01L 2300/0803* (2013.01); *B01L 2300/0861* (2013.01); *B01L 2300/165* (2013.01); *B01L 2400/0406* (2013.01); *B01L 2400/0409* (2013.01); *G01N 2001/149* (2013.01)

(56) References Cited

U.S. PATENT DOCUMENTS

| | | | |
|---|---|---|---|
| 2003/0199894 A1* | 10/2003 | Boecker | A61B 5/15184 606/181 |
| 2005/0178218 A1 | 8/2005 | Montagu | |
| 2005/0198932 A1 | 9/2005 | Franzen et al. | |
| 2006/0084174 A1 | 4/2006 | Ogawa et al. | |
| 2008/0227217 A1 | 9/2008 | Yamamoto et al. | |
| 2009/0162940 A1 | 6/2009 | Wardlaw et al. | |
| 2009/0259146 A1* | 10/2009 | Freeman | A61B 5/15123 600/583 |
| 2012/0000299 A1 | 1/2012 | Buechner | |
| 2012/0271197 A1* | 10/2012 | Castle | A61B 5/150091 600/583 |
| 2013/0261499 A1* | 10/2013 | Kissinger | A61B 5/155 600/573 |
| 2014/0114160 A1* | 4/2014 | Freeman | A61B 5/15161 600/365 |
| 2015/0185233 A1 | 7/2015 | Raiker et al. | |
| 2016/0266099 A1* | 9/2016 | Price | B01L 3/5023 |
| 2017/0120259 A1 | 5/2017 | Takeuchi et al. | |
| 2017/0350910 A1* | 12/2017 | Okamoto | G01N 35/00 |

FOREIGN PATENT DOCUMENTS

| | | |
|---|---|---|
| JP | S457226 | 3/1970 |
| JP | H01199159 | 8/1989 |
| JP | 2001502793 | 2/2001 |
| JP | 2003-185671 | 7/2003 |
| JP | 2004109082 | 4/2004 |
| JP | 2005515065 | 5/2005 |
| JP | 2011-149832 | 8/2011 |
| JP | 2011-179816 | 9/2011 |
| JP | 2012518157 | 8/2012 |
| JP | 2015525888 | 9/2015 |
| WO | 2007052647 | 5/2007 |
| WO | 2016009720 | 1/2016 |

OTHER PUBLICATIONS

"Office Action of Japan Counterpart Application," dated Nov. 7, 2018, with English translation thereof, p. 1-p. 11.
"Office Action of China Counterpart Application," dated Mar. 2, 2020, with English translation thereof, p. 1-p. 12.
"Search Report of Europe Counterpart Application", dated May 6, 2019, p. 1-p. 11.

* cited by examiner

US 10,962,450 B2

SPECIMEN COLLECTION DEVICE, HOLDER FOR SPECIMEN COLLECTION DEVICE, AND SPECIMEN PRE-PROCESSING METHOD THAT USES SPECIMEN COLLECTION DEVICE

CROSS-REFERENCE TO RELATED APPLICATION

This application is a 371 application of the international PCT application serial no. PCT/JP2016/066776, filed on Jun. 6, 2016, which claims the priority benefits of Japan application no. PCT/JP2016/050943, filed on Jan. 14, 2016. The entirety of each of the abovementioned patent applications is hereby incorporated by reference herein and made a part of this specification.

TECHNICAL FIELD

The present invention relates to a sample collection device for collecting a sample and then collecting a desired constant volume of sample component by centrifugation. The present invention also relates to a holder for use in centrifuging or further storing the sample collection device. The present invention also relates to a sample pre-processing method using the sample collection device. The sample includes a liquid sample, such as blood, containing two or more components different in specific gravity.

BACKGROUND ART

When the amount of a blood sample is smaller, it is more difficult to isolate only a plasma component, which is obtained as a supernatant by centrifuging a minute amount of blood contained in a conventional centrifuge tube having a capacity of several milliliters or more, with a micropipette or the like without mixing with a blood cell component.

As a device for collecting a plasma component from a minute amount of blood sample, a micro blood collection tube constituted from a capillary having both open ends is used. When the plasma component is collected with the use of the micro blood collection tube, blood is sucked into the micro blood collection tube, a tip of the micro blood collection tube is sealed with a patty or the like, and the micro blood collection tube is placed in another container and centrifuged. Then, the blood collection tube is cut by snapping off at around an interface between a plasma part and a blood cell part, and only the plasma part is extracted by transferring into a separately-prepared capillary having a given capacity. The extracted plasma component is properly processed and then analyzed by a TLC (thin-layer chromatograph), an LC (liquid chromatograph), an LC/MS (liquid chromatograph/mass spectrometer), a mass spectrometer, or the like.

A centrifuge tube has also been proposed which is intended to collect only a minute amount of white blood cell part obtained by centrifugation as a part located between a blood cell part and a plasma part (see Patent Document 1). The centrifuge tube has two upper and lower reservoirs having a large diameter and a large capacity and a reservoir provided between these two reservoirs so as to have a small diameter and a small capacity. The lower large-capacity reservoir has a bottom, and the upper large-capacity reservoir is opened by providing an opening. When a predetermined amount of blood is collected in the centrifuge tube through the upper opening and then centrifuged, a white blood cell part is contained in the small-capacity reservoir. After the centrifugation, a fine glass tube (capillary) is inserted through the upper opening to collect the white blood cell part contained in the small-capacity reservoir.

Studies have also been actively performed to detect substances by reacting, with reagents, the substances contained in a blood component obtained by introducing blood into a disc having several flow channels including capillaries and centrifuging the disc to separate the blood into its components. As an apparatus used for such a purpose, for example, an apparatus has been proposed which comprises a disc-shaped member having a chamber, pathways, a reservoir, and analysis cells which are integrally formed therein (see Patent Document 2). A blood sample is introduced into the apparatus and centrifuged to separate blood cells from serum. Then, the serum is subjected to several processes or tests.

PRIOR ART DOCUMENTS

Patent Documents

Patent Document 1: Japanese Patent Laid-open Publication No. H01-199159
Patent Document 2: Japanese Translation of PCT International Application Publication No. 2001-502793

SUMMARY OF THE INVENTION

Problems to be Solved by the Invention

In a preclinical study performed for drug development, the amount of blood obtained from a small animal is limited. Therefore, it is difficult to perform sampling from a single small animal at all time points to collect blood samples required for toxicokinetics and pharmacokinetics analysis. Therefore, a drug is administered to several small animals, and then blood samples at different time points are collected from different individuals. In recent years, measuring apparatuses have been improved to have a very high sensitivity, and therefore, only a very minute amount of sample is required for measurement. If a constant volume of plasma or serum required for measurement can be directly and simply obtained from a minute amount of blood, the amount of a blood sample required for measurement can be significantly reduced. This contributes to a reduction in the number of sacrificed animals and, in addition, makes it possible to obtain a series of samples from a single small animal to remove variance caused by individual differences from measurement data. Further, also in clinical tests and medical settings, collection of a large amount of blood sample using a needle can be changed to simple collection of a blood sample from a peripheral blood vessel in the ear, hand, or abdomen, which contributes to a significant reduction of the burden of blood collection on infants, children, or patients.

However, when blood is centrifuged using such a micro blood collection tube having both open ends as described above instead of a centrifuge tube, it is absolutely necessary to seal one of the ends of the tube with patty or the like and to place the tube in another container. A sample to which the present invention is applied is not limited to blood. The present invention is applied to any liquid sample having two or more components different in specific gravity.

It is an object of the present invention to provide a sample collection device that is simply capable of sucking a sample thereinto, being centrifuged, and collecting a constant volume of predetermined sample component separated by centrifugation; a holder dedicated for the sample collection device; and a sample pre-processing method using the sample collection device.

Solutions to the Problems

A sample collection device according to one embodiment of the present invention comprises a device main body and a flow channel through which a sample is sucked into the device main body by capillary action. The device main body has a proximal end and a distal end, and has an opening provided as a sample suction port on a proximal side thereof. The flow channel provided in the device main body has a thickness small enough to suck a sample by capillary action. The flow channel has two channels that are connected to each other on a distal side of the device main body and that extend from the distal side toward the proximal side of the device main body. One of the channels communicates with the sample suction port, and another channel terminates before reaching the proximal end.

The sample collection device further comprises an air hole necessary for sucking a sample by capillary action, and the air hole communicates with a terminal of the another channel.

The sample collection device further comprises at least one extraction part for collecting a predetermined amount of sample. The at least one extraction part includes a portion of the two channels located on a distal side of the air hole of the device main body. The at least one extraction part can be cut off from the rest of the device main body by cutting grooves.

A holder according to one embodiment of the present invention is a dedicated holder for use in centrifuging or further holding and storing the sample collection device according to one embodiment of the present invention. The holder comprises a disc-shaped supporter, at least one recess that is provided in a surface of the supporter to fit and hold the sample collection device according to one embodiment of the present invention therein in such a manner that the proximal end of the device main body faces a center of a disc of the supporter, and an attaching part that is provided in the supporter to attach the supporter to a centrifuge.

A sample pre-processing method according to one embodiment of the present invention is a method for pre-processing a sample using the sample collection device according to one embodiment of the present invention, comprising following steps of:

(A) using the sample collection device according to one embodiment of the present invention to suck a sample into the flow channel through the sample suction port by capillary action;

(B) then holding the sample collection device in the holder according to one embodiment of the present invention and centrifuging the sample collection device in such a manner that centrifugal force acts in a direction from the proximal end toward the distal end of the device main body; and (C) cutting off the extraction part from the device main body after the centrifugation and placing the at least one extraction part in a reaction container together with a pre-processing liquid to perform pre-processing.

Effects of the Invention

According to the present invention, it is possible to centrifuge a minute amount of sample without either sealing with patty or the like or placing in another container to extract a predetermined component separated by centrifugation as a sample.

EMBODIMENTS OF THE INVENTION

Figure 1A:
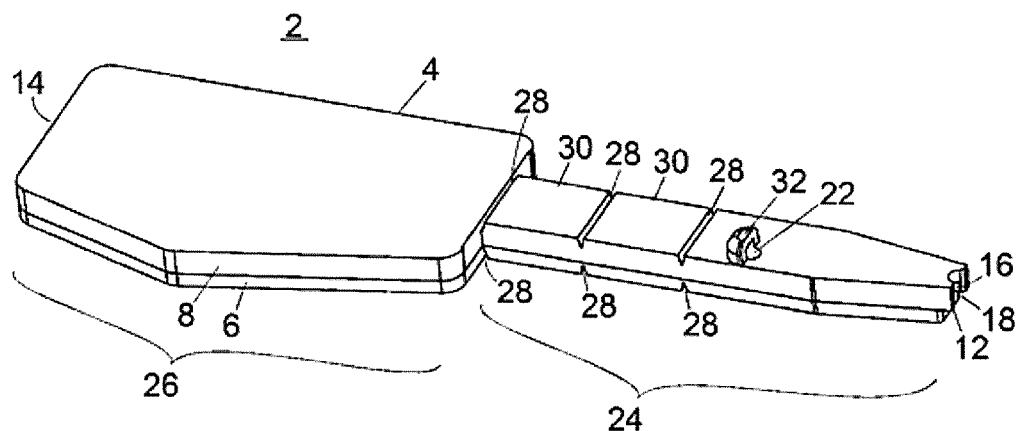
FIG. 1A is a perspective view of a first embodiment of a sample collection device.

In a sample collection device according to one embodiment, a position of an at least one extraction part is preferably determined so that when blood collected as a sample is centrifuged in such a manner that centrifugal force acts in a direction from a proximal end toward a distal end of a device main body, a plasma component or a serum component is contained in a flow channel included in the at least one extraction part. When centrifuged, blood collected as a sample is separated so that a blood cell part and a plasma component or a serum component contained in the two channels are located on a distal side and a proximal side of the device main body, respectively. In order to collect the plasma component or the serum component, the at least one extraction part is provided in a position where the plasma component or the serum component is contained in the channels.

In order to allow the at least one extraction part to collect the plasma component, an anticoagulant may be added to a blood sample. In order to extract plasma from blood directly collected from an individual with the use of the sample collection device, an anticoagulant that prevents the coagulation of blood is preferably provided on an inner surface of the flow channel. The inner surface of the flow channel may be coated with EDTA (ethylenediaminetetraacetic acid) or heparin as anticoagulant.

Part of the sample whose volume corresponds to a volume of a portion of one of the channels located between a position corresponding to an air hole of the other channel and the sample suction port is discharged through the air hole during centrifugation. When a thickness of the portion of the one of the channels is smaller than that of the rest of the flow channel, the portion of the one of the channels can be made longer than when the thickness of the portion of the one of the channels is the same as that of the rest of the flow channel on condition that the volume of the portion of the one of the channels is the same. This improves operability at the time when a sample is collected by suction. Further, it becomes easy to hold a portion of the device main body having the portion of the one of the channels when the at least one extraction part is separated from the rest of the device main body by cutting at the cutting grooves. This also improves operability at the time when the at least one extraction part is separated from the rest of the device main body.

When the cutting grooves comprise three or more cutting grooves provided at regular intervals along a direction from the distal end toward the proximal end of the device main body, the at least one extraction part comprises two or more extraction parts, and therefore, the same two or more sample pieces can be prepared. Further, when the two channels passing through the at least one extraction part have the same thickness and are integrally formed so as to be separable from each other by cutting as well, the same two sample pieces can be prepared. When the same two or more sample pieces are prepared, reanalysis can be performed even when any problems occur in the first analysis.

When the flow channel has a hydrophilic inner surface and blood or an aqueous solution is collected as a sample, the sample can be easily sucked into the flow channel by capillary action. Since the at least one extraction part is cut off from the device main body and is used as a sample piece, the sample collection device is disposed of after each sampling. Therefore, from the viewpoint of cost, the sample collection device is preferably made of plastic. In general, plastic is hydrophobic, and therefore, the inner surface of the flow channel is subjected to hydrophilic treatment so as to be hydrophilic. Examples of the hydrophilic treatment include, but are not limited to, plasma treatment, ultraviolet irradiation, and coating with a hydrophilic polymer. The hydrophilic treatment is not particularly limited as long as it is performed by a conventional method.

On a surface of the device main body in which the air hole is provided, a cover is preferably provided which covers the distal side of the air hole. When the sample collection device is centrifuged after a sample is sucked into the flow channel in such a manner that centrifugal force acts in a direction from the proximal end toward the distal end of the device main body, part of the sample is discharged through the air hole because the sample reaches equilibrium. Since the at least one extraction part is provided on the distal side of the air hole and centrifugal force acts on the distal side of the device main body, the discharged sample tends to move toward the at least one extraction part. However, when the cover that covers the distal side of the air hole is provided, it is possible to prevent the discharged sample from adhering to the at least one extraction part.

Alternatively, discharge of a sample through the air hole due to centrifugal force during centrifugation may be prevented. The reason why a sample is discharged through the air hole when the sample reaches equilibrium during centrifugation is that when the sample collection device is centrifuged in a state where the position of the end of the sample in one of the channels and the position of the end of the sample in the other channel are different, a surplus of the sample is generated and discharged through the air hole when the sample reaches equilibrium.

Therefore, a liquid reservoir may be provided at the terminal of the other channel. The liquid reservoir has a thickness large enough to prevent a sample from being sucked by capillary action. When the liquid reservoir having the thickness large enough to prevent the sample from being sucked by capillary action is provided at the terminal of the other channel, the sample sucked through the sample suction port stops at an entrance of the liquid reservoir. Since the entrance of the liquid reservoir is located on the distal side of the air hole, it is possible to stop a sample sucked through the sample suction port at a position located on the distal side of the air hole. When the sample collection device is centrifuged in such a state, at least part of a surplus of the sample generated when the sample reaches equilibrium by centrifugal force is stored in the liquid reservoir, which prevents or reduces the discharge of the sample through the air hole.

An amount of the surplus sample generated when a sample reaches equilibrium during centrifugation is equal to the internal capacity of a portion of the one of the channels located on the proximal side of the position corresponding to the terminal of the other channel. Therefore, when provided at the terminal of the other channel, the liquid reservoir preferably has the internal capacity equal to or larger than that of the portion of the one of the channels located on the proximal side of a position corresponding to the terminal of the other channel. This makes it possible to store all the surplus sample generated when a sample reaches equilibrium during centrifugation in the liquid reservoir to prevent the discharge of the sample through the air hole.

Further, the liquid reservoir may have a hydrophobic inner surface. When the liquid reservoir has a hydrophobic inner surface, a sample that has reached the entrance of the liquid reservoir is less likely to enter the liquid reservoir. This makes it possible, when the sample is sucked, to more reliably stop the sample at the entrance of the liquid reservoir.

Further, the sample collection device according to the present invention has a feature that the at least one extraction part can be cut off from the rest of the device main body. However, there is a fear that when the at least one extraction part is cut off from the rest of the device main body, a sample contained in the channels passing through the at least one extraction part leaks from the cut surface of the flow channel. Therefore, a portion of the channels passing through the at least one extraction part, which passes through each of the cutting grooves at which the at least one extraction part is cut off from the rest of the device main body, preferably has a thickness smaller than that of the rest of the channels. This makes it difficult for the sample contained in the channels passing through the at least one extraction part to leak from the cut surface of the flow channel when the at least one extraction part is cut off from the rest of the device main body.

The device main body preferably has, on the distal side of the at least one extraction part, a wide section whose width is larger than that of the at least one extraction part. In this case, an information about the sample can be written on the wide section, or a label containing information about the sample can be attached to the wide section. However, it is not always necessary to provide such a wide section, and when the sample collection device is required to be made smaller, the width of the distal side of the device main body may be the same as that of the at least one extraction part.

In the holder according to one embodiment, an at least one recess that holds the sample collection device comprises a plurality of recesses radially provided in a supporter. This makes it possible to centrifuge the sample collection devices at the same time. Further, such holder is suitable for efficient storage such as the storage of the sample collection devices in the holders different from individual to individual.

Further, in the holder according to one embodiment, an attaching part for attaching the holder to a centrifuge preferably has a through hole provided at a center of the supporter so that two or more stacked holders are attached to the centrifuge via the through holes. When the two or more holders are stacked, the sample collection devices held in the holder other than an uppermost holder are covered by the other holder stacked on the holder, and are therefore prevented from being thrown out by centrifugal force. The uppermost holder may be covered by stacking an empty holder holding no sample collection device or a plate material large enough to cover the sample collection devices thereon as a cover.

In the sample pre-processing method according to one embodiment, when blood is collected as a sample, it is preferred that after the step (C), an organic solvent is further added and deproteinization is performed by centrifugation.

A sample collection device according to a first embodiment is shown in FIGS. 1A and 1B and FIGS. 2A and 2B.

A sample collection device 2 comprises a device main body 4, and the device main body 4 is constituted from a lower substrate 6 and an upper substrate 8. The lower substrate 6 and the upper substrate 8 are integrated by bonding to form the device main body 4. In a surface of the upper substrate 8 to be bonded, a flow channel 10 for sample collection is formed. Since the lower substrate 6 and the upper substrate 8 are bonded together, the flow channel 10 is provided in the device main body 4.

The device main body 4 has a proximal end 12 and a distal end 14. The sample collection device 2 is used to suck a sample and is then subjected to centrifugation. At the time of centrifugation, the sample collection device 2 is placed in a centrifuge in such a manner that a centrifugal force acts in a direction from the proximal end 12 toward the distal end 14. The proximal end 12 and distal end 14 of the device main body 4 are based on the direction of the centrifugal force.

The device main body 4 has a sample suction port 16 on a proximal side thereof. The sample suction port 16 is provided as an opening that communicates with a recess 18 provided at the proximal end 12 of the device main body 4. The recess 18 is intended to make it easy to suck a sample, such as blood, through the sample suction port 16 when the proximal end 12 is brought into contact with the sample for sample collection.

The flow channel 10 has a thickness small enough to suck the sample by capillary action. The flow channel 10 has two channels 10a and 10b that are connected to each other at a junction 20 located on a distal side of the device main body 4 and that extend from the distal side toward the proximal side of the device main body 4. One of the channels 10a has an introduction channel 10c, and the introduction channel 10c communicates with the sample suction port 16. The other channel 10b terminates before reaching the proximal end 12. At the terminal of the other channel 10b, an air hole 22 is provided which acts as an air outlet when a sample is sucked into the flow channel 10 by capillary action. The air hole 22 is formed as a through hole penetrating the upper substrate 8.

The introduction channel 10c has a thickness smaller than that of the rest of the channel 10a.

A position of a distal end of the introduction channel 10c in the channel 10a and a position of a proximal end of the channel 10b are substantially the same. When sucked into the flow channel 10 by capillary action, the sample is contained in almost the entire flow channel 10. When the sample collection device 2 is centrifuged in such a state, the sample remains in a portion of the flow channel 10 from the distal end of the introduction channel 10c to the air hole 22 so that the flow channels 10a and 10b are filled with the sample and the introduction channel 10c is empty.

The device main body 4 includes a collection section 24 provided on the proximal side thereof so as to have a small width, and a wide section 26 having a width larger than that of the collection section 24.

The collection section 24 has extraction parts 30. The extraction parts 30 are provided on a distal side of the air hole 22, and can be cut off by cutting grooves 28. In this embodiment, the cutting grooves 28 are provided by forming grooves so that portions of the device main body 4 where the cutting grooves 28 are provided are thinner than the rest of the device main body 4. Each of the extraction parts 30 is defined by the two cutting grooves 28 parallel to each other. The cutting grooves 28 are formed in a direction orthogonal to a longitudinal direction of the collection section 24 (i.e., in a direction from the proximal end 12 toward the distal end 14) so as to extend over the entire width of the collection section 24. Each of the extraction parts 30 includes the two channels 10a and 10b. The cutting grooves 28 are not limited to those provided by forming grooves as used in this embodiment as long as they have a lower strength so as to be snapped off with fingers. For example, the cutting grooves 28 may have a smaller width.

The grooves for providing the cutting grooves 28 are preferably formed on both upper and lower sides of the collection section 24, that is, on both front and back sides of the collection section 24 as in this embodiment.

The channels 10a and 10b do not need to have a uniform thickness over the entire length thereof. For example, a length of the wide section 26 can be made smaller by making the thickness of the flow channel 10 passing through the wide section 26 larger than that of the flow channel 10 passing through the collection section 24. In the cases of this embodiment and the next second embodiment, the extraction part 30 including the two channels 10a and 10b therein is directly used as an analytical sample. The channels 10a and 10b included in the extraction part 30 do not need to have the same thickness, but when the channels 10a and 10b included in the extraction part 30 have the same thickness, the sample collection device 2 can be more easily designed. However, in the case of a third embodiment that will be described later, the channels 10a and 10b included in the extraction part 30 are separated from each other and are used as individual analytical samples. In this case, the channels 10a and 10b included in the extraction part 30 preferably have the same thickness.

The extraction parts 30 of the collection section 24 are located on the proximal side of the device main body. Therefore, when a collected sample is centrifuged, a component having a smaller specific gravity obtained by centrifugation is contained in the extraction parts 30. For example, the position of the extraction parts 30 is determined so that when blood collected as a sample is centrifuged in such a manner that centrifugal force acts in a direction from the proximal end 12 toward the distal end 14 of the device main body 2, a plasma component or a serum component is contained in the flow channel 10 included in the extraction parts 30.

The sample collection device according to the present invention has at least one extraction part 30. In this embodiment, three cutting grooves 28 are provided at regular intervals along a direction from the distal end 14 toward the proximal end 12 of the device main body 4 so that two extraction parts 30 are provided. The cutting grooves 28 may be provided so that 3 or more extraction parts 30 are provided. When two or more extraction parts 30 are provided, analysis can be performed more than once using the same sample. This is advantageous in that reanalysis can be performed when any problems occur in the first analysis. The obtained two or more extraction parts 30 have a same length so that a same amount of the sample is contained in the flow channel 10 passing through each of the extraction parts 30, which makes it possible to quantitatively perform reanalysis.

The wide section 26 is large enough to write an identification information such as a name or a number of the sample collected in this sample collection device or to attach a label with such identification information. The wide section 26 can also be used as a gripping area to hold the sample collection device.

In this embodiment, the wide section 26 has a larger thickness than the collection section 24, which makes it easy to hold the wide section 26. However, the wide section 26 may have a same thickness as the collection section 24.

On the surface of the collection section 24 in which the air hole 22 is provided, a cover 32 is provided. The cover 32 covers a distal portion of the air hole 22. The cover 32 is configured to upwardly extend from a position near the distal end of the air hole 22 so that an area above the distal portion of the air hole 22 is covered and a proximal portion of the air hole 22 is opened. By providing the cover 32, it is possible to prevent a sample discharged to the outside from the flow channel 10 through the air hole 22 from moving toward a distal side of the air hole 22 during centrifugation. This makes it possible to prevent the sample from adhering to a surface of the extraction parts 30 because the extraction parts 30 are provided on the distal side of the air hole 22.

The sample collection device 2 is made of, for example, a resin material. The resin material is not particularly limited, and may be, for example, COP (cycloolefin polymer), PMMA (polymethyl methacrylate resin), PP (polypropylene resin), PC (polycarbonate resin), or PVA (polyvinyl alcohol).

A method for bonding together the lower substrate 6 and the upper substrate 8 is not particularly limited, either. Examples of the method include one in which the lower substrate 6 and the upper substrate 8 are bonded together by heating and one in which the lower substrate 6 and the upper substrate 8 are bonded together by activating their surfaces to be bonded by plasma treatment.

The flow channel 10 sucks a liquid sample through the suction port 16 by capillary action, and therefore, the flow channel 10 needs to have a cross-sectional area small enough to cause capillary action. In addition, when the sample is blood or an aqueous solution, the flow channel 10 needs to have a hydrophilic inner surface. The resin material exemplified above is hydrophobic, and therefore, an inner surface of the flow channel 10 and the suction port 16 are preferably treated so as to be hydrophilic.

When blood is collected as the sample, an anticoagulant that prevents the coagulation of blood is preferably provided on the inner surface of the flow channel 10 in order to directly suck blood from an individual and collect plasma in the extraction part 30 by centrifugation. The anticoagulant may be coated on a hydrophilic polymer coating provided on the inner surface of the flow channel 10.

Figure 3A:
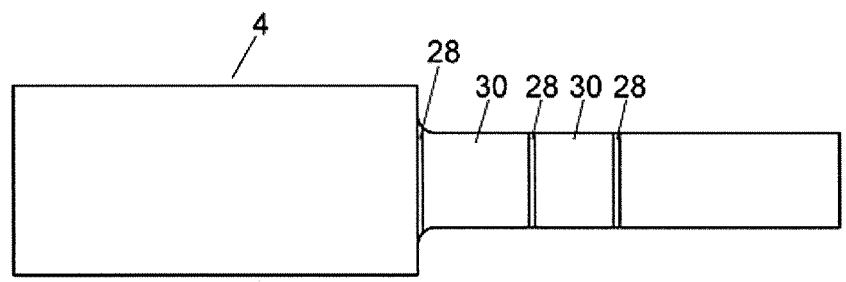
FIG. 3A is a schematic plan view of the first embodiment.
Figure 3B:
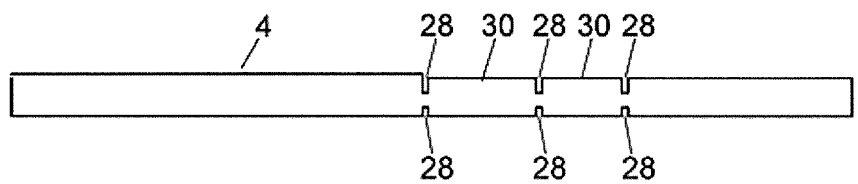
FIG. 3B is a schematic front view of the first embodiment.
Figure 3C:
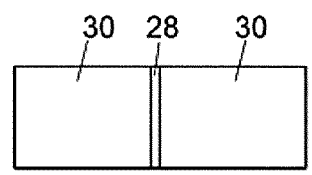
FIG. 3C is a schematic plan view of two extraction parts cut off from a device main body of the first embodiment.
Figure 3D:
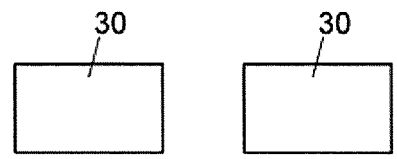
FIG. 3D is a schematic plan view showing a state where the two extraction parts of the first embodiment are separated from each other.

The extraction parts 30 are cut off from the device main body 4 of the sample collection device 2 after centrifugation in order to use the extraction parts 30 for analysis. As shown in FIG. 3C, the two extraction parts 30 connected to each other are cut off from the device main body 4 shown in the schematic diagrams of FIGS. 3A and 3B at the cutting grooves 28 provided at the both ends thereof. Then, as shown in FIG. 3D, the two extraction parts 30 are separated from each other by cutting at the cutting area 28 provided therebetween to obtain the two individual extraction parts 30. The extraction parts 30 can be cut off from the device main body 4 by snapping off the device main body 4 at the cutting grooves 28 with fingers. In this way, two analytical samples can be obtained from one device main body 4.

Figure 4A:
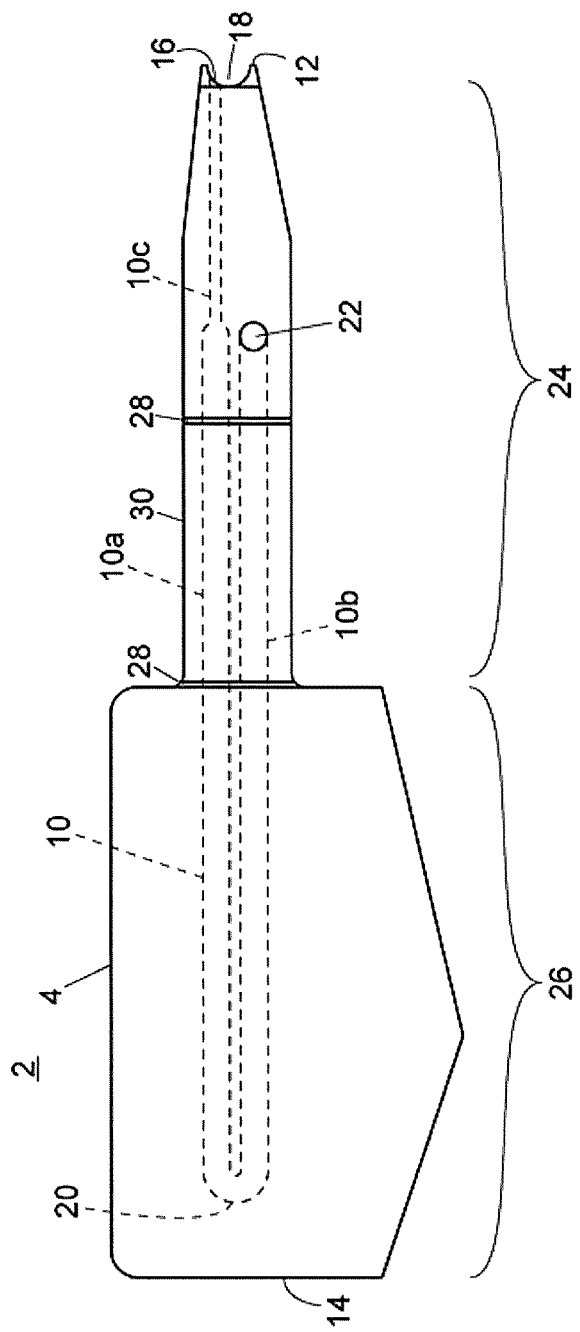
FIG. 4A is a schematic plan view of a second embodiment of the sample collection device.
Figure 4B:
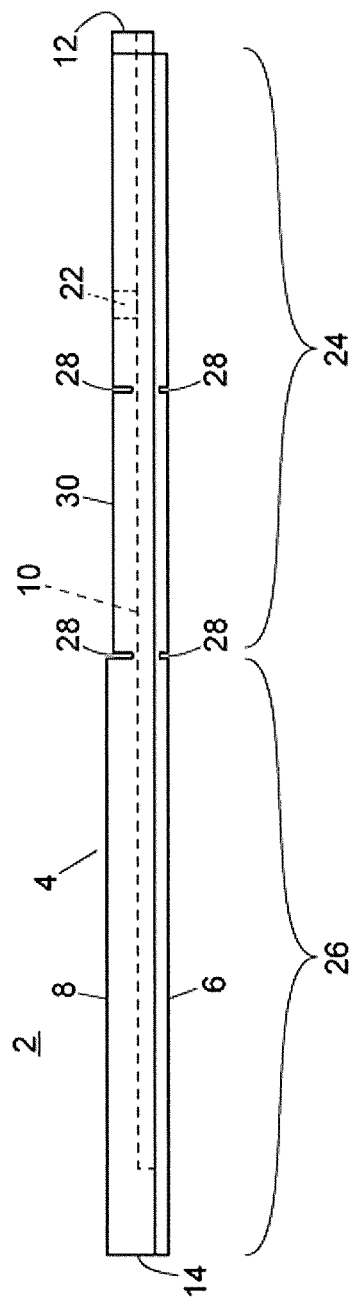
FIG. 4B is a schematic front view of the second embodiment.

A second embodiment is shown in FIG. 4A and FIG. 4B. This embodiment is different from the first embodiment in that the number of the extraction parts 30 is one. The configuration of the second embodiment other than the above is the same as that of the first embodiment. Also in this embodiment, the cover 32 that covers an area above the distal portion of the air hole 22 is preferably provided.

Figure 5A:
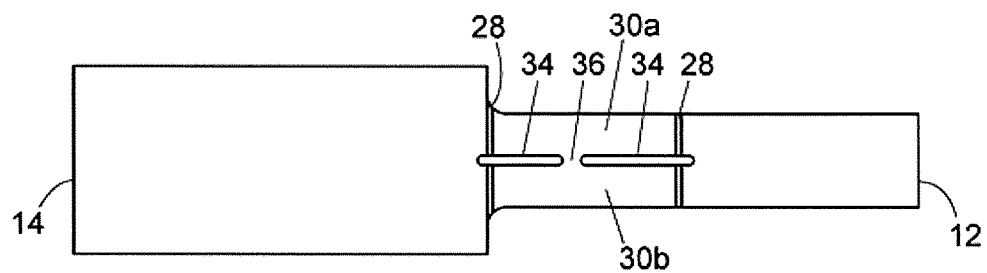
FIG. 5A is a schematic front view of a third embodiment of the sample collection device.
Figure 5B:
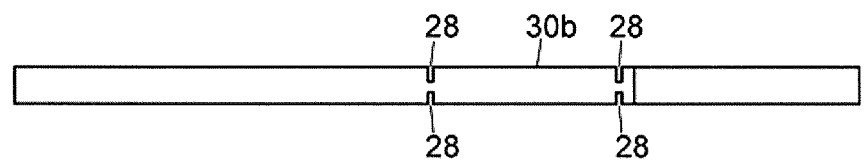
FIG. 5B is a schematic front view of the third embodiment.

A third embodiment is shown in FIG. 5A and FIG. 5B. The third embodiment is different from the second embodiment in that the extraction part 30 can be separated into a portion 30a through which the channel 10a passes and a portion 30b through which the channel 10b passes. The configuration of the third embodiment other than the above is the same as that of the second embodiment. In order to allow the extraction part 30 to be separated into the portion 30a and the portion 30b, the extraction part 30 is provided with a cutting area 36. The cutting area 36 is provided by forming slits 34 and 34 along the channels 10a and 10b so that part of the material of the device main body 4 remains.

Figure 5C:
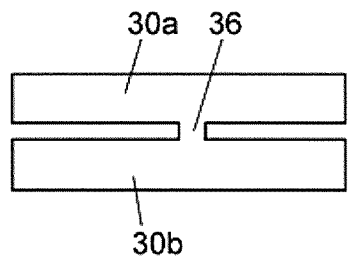
FIG. 5C is a schematic plan view of an extraction part cut off from a device main body of the third embodiment.
Figure 5D:
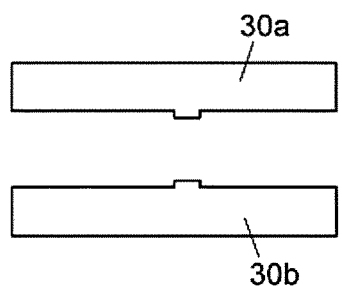
FIG. 5D is a schematic plan view showing a state where the extraction part cut off from the device main body of the third embodiment is separated into two portions each including a channel.

As shown in FIG. 5C, the extraction part 30 is cut off from the device main body 4 after centrifugation in order to use the extraction part 30 for analysis. First, the extraction part 30 is cut off from the device main body 4 by snapping off the device main body 4 at the cutting grooves 28 with fingers. Then, as shown in FIG. 5D, the extraction part 30 is snapped off at the cutting area 36 to separate the portion 30a and the portion 30b from each other. In this way, two analytical samples can be obtained from one extraction part 30.

In the case of this embodiment, each of the portion 30a including the channel 10a and the portion 30b including the channel 10b is used as an analytical sample. Therefore, the channels 10a and 10b included in the extraction part 30 preferably have a same length and width to quantitatively perform reanalysis or the like.

Also in this embodiment, the cover 32 that covers an area above the distal portion of the air hole 22 is preferably provided.

In these embodiments, the channels 10a and 10b have a width of, for example, 0.6 mm and a depth of, for example, 1 mm so as to be able to suck a liquid by capillary action. These dimensions are merely examples, and are not particularly limited as long as a liquid can be sucked by capillary action. The length of the channel 10a and the length of the channel 10b may be determined by the amount of a sample to be sucked. For example, the total length of the channel 10a and the channel 10b is 25 mm. The width and depth of the channel 10c are smaller than those of the channels 10a and 10b. Each of the channels has a surface subjected to hydrophilization treatment.

For example, when the quantitative analysis of blood is performed, 10 µL is regarded as an appropriate amount of sample. Therefore, the extraction part 30 or the portion 30a or 30b preferably has a size such that the amount of plasma or serum collected in the flow channel 10 or the channel 10a or 10b included in the extraction part 30 or the portion 30a or 30b is 10 µL. Further, when the extraction part 30 or the portion 30a or 30b is to be placed in a reaction container such as a centrifuge tube to be attached to the centrifuge for pre-processing a collected sample, the extraction part 30 or the portion 30a or 30b preferably has a size in such a way that it can be placed in the reaction container.

Figure 7A:
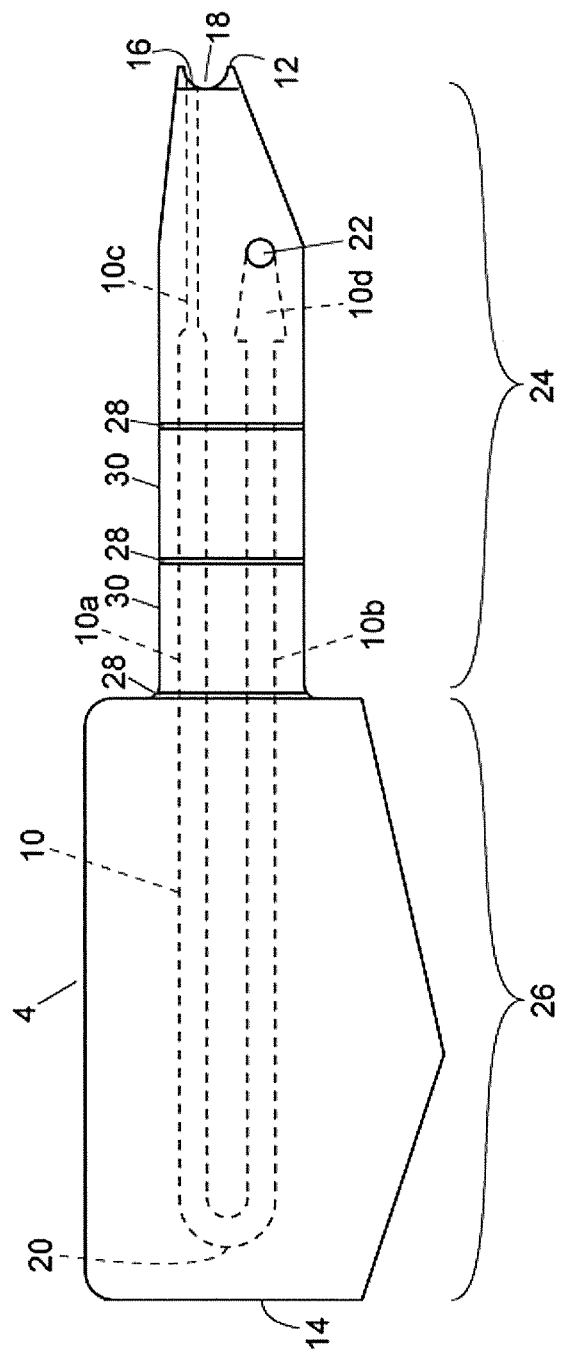
FIG. 7A is a schematic plan view of a fourth embodiment of the sample collection device.
Figure 7B:
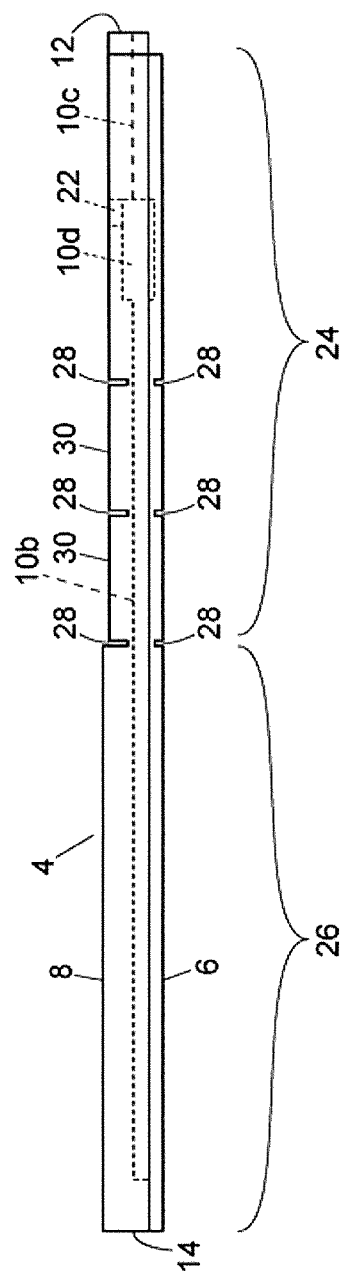
FIG. 7B is a schematic front view of the fourth embodiment.

A fourth embodiment is shown in FIG. 7A and FIG. 7B. The feature of this embodiment is that a liquid reservoir 10d is provided at a terminal of the channel 10b. At least an entrance (distal end) of the liquid reservoir 10d has a cross-sectional area large enough to prevent a liquid from being sucked by capillary action, and the air hole 22 communicates with a proximal end of the liquid reservoir 10d. The liquid reservoir 10d has an internal capacity equal to or larger than that of a portion of the introduction channel 10c of the channel 10a located on the proximal side (i.e., on the upper side in the drawing) of a position corresponding to the air hole 22.

The cross-sectional area of the entrance of the liquid reservoir 10d is, for example, twice or more that of the rest of the channel 10b. For example, the cross-section of the entrance of the liquid reservoir 10d has a width of about 3 mm and a depth of about 1.5 mm.

The advantage of providing the liquid reservoir 10d at the terminal of the channel 10b is as follows.

First, since the liquid reservoir 10d does not suck a sample by capillary action, a sample sucked through the sample suction port 16 stops at the entrance of the liquid reservoir 10d without reaching the air hole 22. This makes it possible to collect a desired amount of sample in the channels 10a and 10b without increasing the amount of a sample collected in the flow channel 10.

Further, since the sample sucked through the sample suction port 16 stops at the entrance of the liquid reservoir 10d, the liquid reservoir 10d does not contain the sample before centrifugation is performed. It is to be noted that when the inner surface of the liquid reservoir 10d is made hydrophobic, the sample can be more reliably stopped at the entrance of the liquid reservoir 10d. When centrifugation is performed in such a state, a surplus of the sample generated when the sample reaches equilibrium is stored in the liquid reservoir 10d. Since the liquid reservoir 10d has an internal capacity equal to or larger than that of a portion of the introduction channel 10c of the channel 10a located on the proximal side (i.e., on the upper side in the drawing) of a position corresponding to the air hole 22, all the surplus sample is stored in the liquid reservoir 10d. This makes it possible to prevent or reduce the discharge of the surplus sample from the channel 10b through the air hole 22.

Figure 1B:
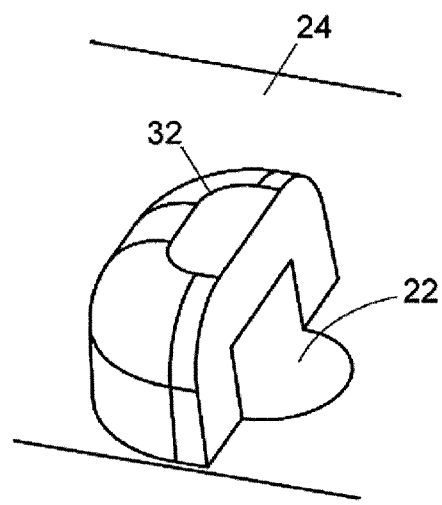
FIG. 1B is an enlarged perspective view of an upper substrate of the first embodiment.
Figure 2A:
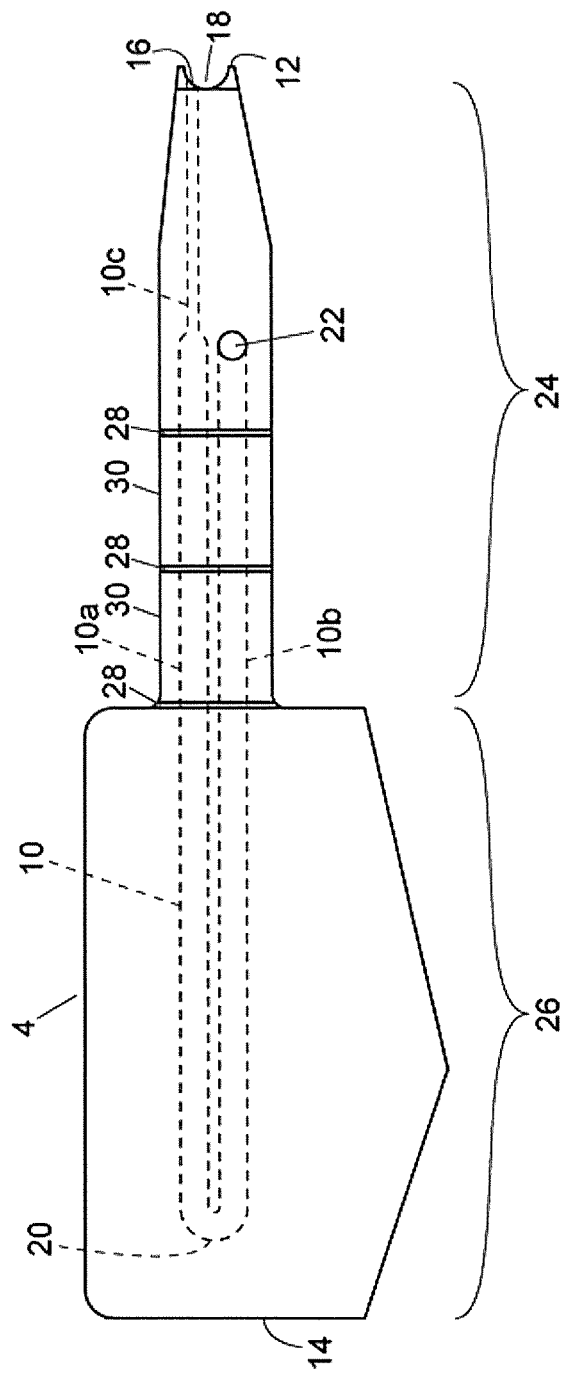
FIG. 2A is a schematic plan view showing the position of a flow channel of the first embodiment.
Figure 2B:
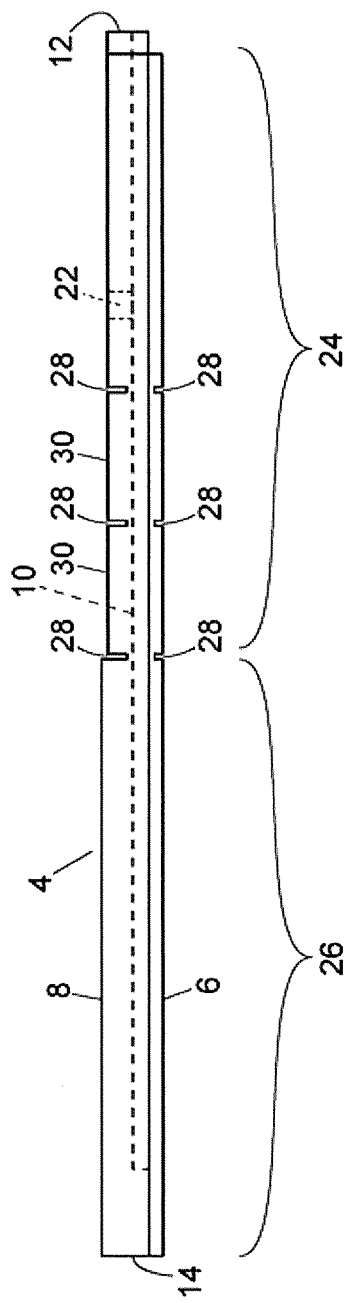
FIG. 2B is a schematic front view of the first embodiment.

It is to be noted that although not shown in the embodiments, a cover that prevents the scattering of the sample discharged through the air hole 22, such as the cover 32 shown in FIG. 1B, may be provided also in this embodiment. Further, similarly to the second embodiment described above, the number of the extraction parts 30 may be one. Further, similarly to the third embodiment, the extraction part 30 may be configured to be separable into a portion 30a through which the channel 10a passes and a portion 30b through which the channel 10b passes.

Figure 8:
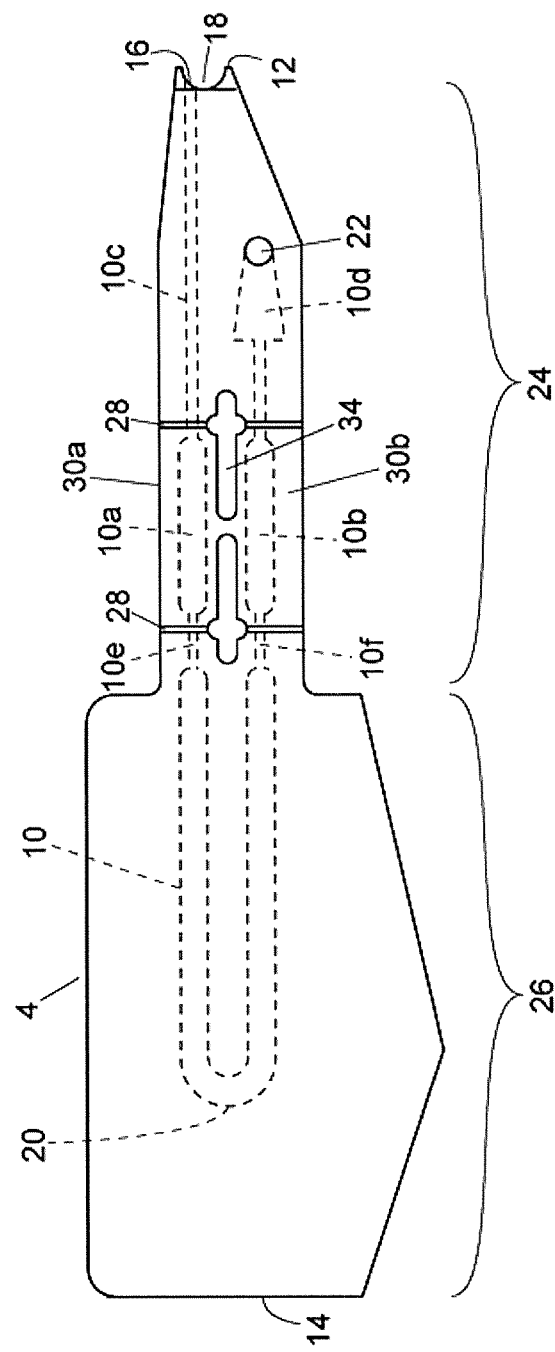
FIG. 8 is a schematic plan view of a fifth embodiment of the sample collection device.

A fifth embodiment is shown in FIG. 8. The feature of this embodiment is that a portion 10e of the channel 10a and a portion 10f of the channel 10b which pass through the cutting area 28 for cutting off the extraction part 30 (30a and 30b in FIG. 8) are made thinner than the rest of the two channels 10a and 10b passing through the extraction part 30 (30a and 30b in FIG. 8). A cross-sectional area of each of the thinner portions 10e and 10f is, for example, one-half or less of that of the rest of the channels 10a and 10b passing through the extraction part 30. For example, each of the portions 10e and 10f has a width of about 0.4 mm and a depth of about 0.6 mm. The configuration of the fifth embodiment other than the above may be the same as that of any one of the first to fourth embodiments.

Since the portion 10e of the channel 10a and the portion 10f of the channel 10b which pass through the cutting area 28 for cutting off the extraction part 30 (30a and 30b in FIG. 8) are thinner than the rest of the two channels 10a and 10b passing through the extraction part 30 (30a and 30b in FIG. 8), a sample is less likely to leak from the end of the flow channel when the extraction part 30 (30a and 30b in FIG. 8) is cut off from the rest of the device main body 4. As a result, the quantitativity of the extraction part 30 is improved.

Figure 6A:
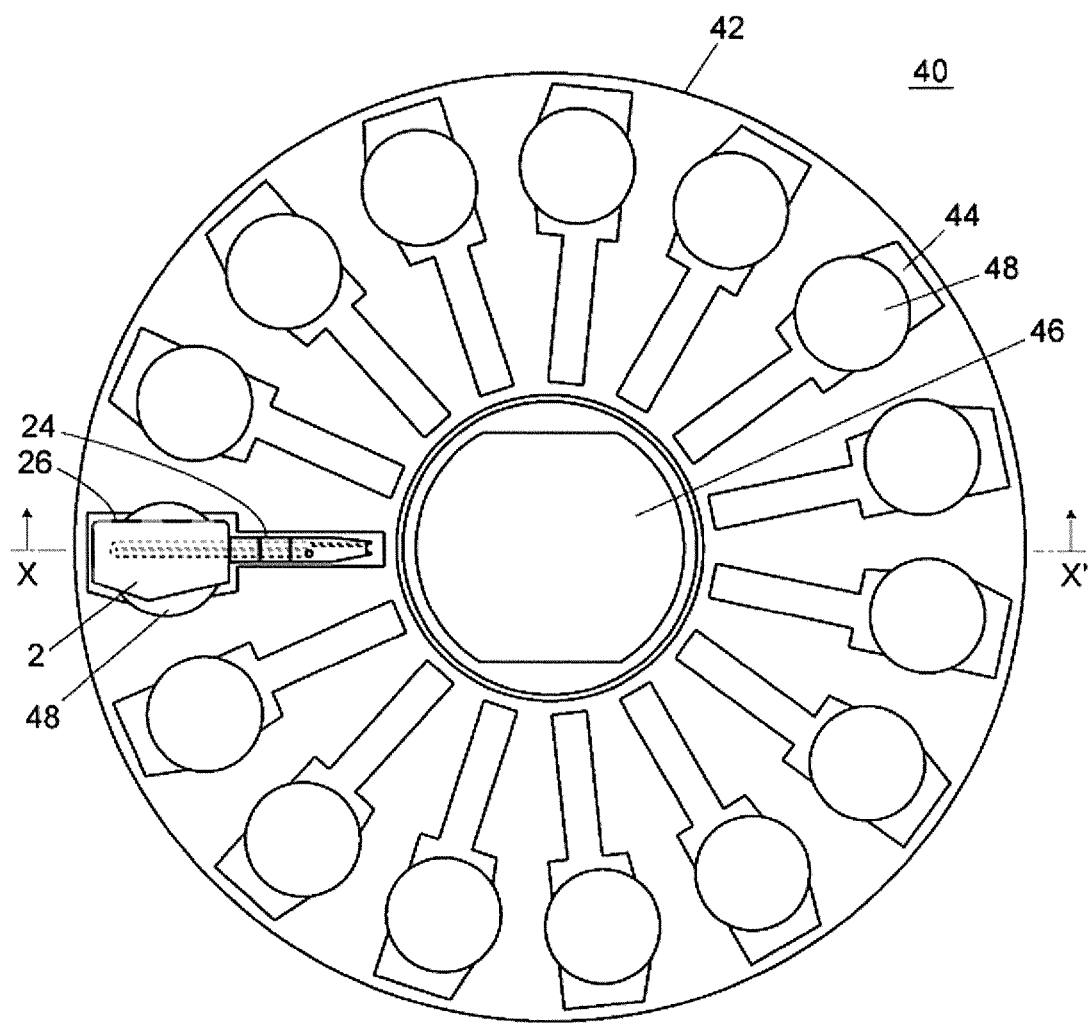
FIG. 6A is a schematic plan view of an embodiment of a holder.
Figure 6B:
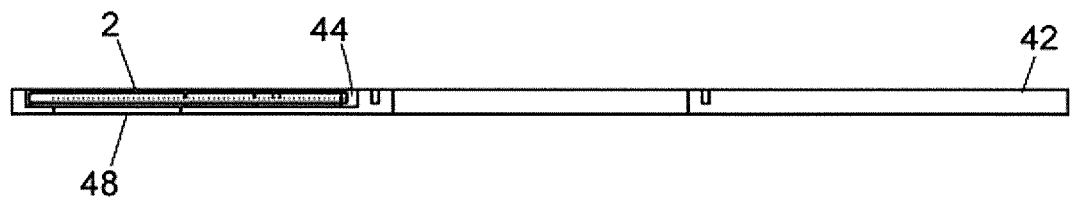
FIG. 6B is a sectional view of the embodiment taken along a line X-X' in FIG. 6A.

As shown in FIG. 6A and FIG. 6B, a holder 40 according to an embodiment of the present invention comprises a disc-shaped supporter 42. The disc-shaped supporter 42 has a plurality of recesses 44 radially arranged therein. Each of the recesses 44 is used to hold the sample collection device 2 fitted therein. FIG. 6A and FIG. 6B show a state in which the sample collection device 2 is fitted in one of the recesses 44. When the holder 40 is used for centrifugation or storage of the sample collection device 2, the sample collection devices 2 are generally fitted and held in more than one or all of the recesses 44. In this embodiment, the number of the recesses 44 is 15. However, the number of the recesses 44 is not particularly limited, and a desired number of recesses may be provided. The holder 40 that can hold a larger number of the sample collection devices 2 is advantageous in that a larger number of the sample collection devices 2 can be centrifuged at one time, or a large number of the sample collection devices 2 can be stored in a smaller space when the sample collection devices 2 are held in the holder 40 during storage.

The holder 40 has a hole 46 provided at the center thereof as an attaching part. The hole 46 is used to attach the holder 40 to a centrifuge. The shape of the hole 46 corresponds to that of a rotary shaft of a centrifuge to be used so that the rotary shaft is inserted into the hole 46. This makes it possible to rotate the holder 40 together with the rotary shaft. The shape of the hole 46 as the attaching part is determined on the basis of a centrifuge to be used. When the centrifuge to be used has a positioning pin at a position corresponding to a periphery of the supporter 42, the holder 40 can have a circular hole provided at the center thereof to allow a rotary shaft to pass through and a notch provided at the peripheral position thereof corresponding to the position of the positioning pin.

As shown on the left side of FIG. 6A, a planar shape of each of the recesses 44 of the holder 40 corresponds to a shape of the sample collection device 2. An orientation of each of the recesses 44 is determined in such a manner that a direction connecting the proximal end and the distal end of the sample collection device 2 held in the recess 44 corresponds to a radial direction of the holder 40, the proximal end of the sample collection device 2 faces the center of the holder 40, and the distal end of the sample collection device 2 faces outwardly in the radial direction of the holder 40.

A depth of each of the recess 44 may be smaller than the thickness of the sample collection device 2 as long as the sample collection device 2 held in the recess 44 is not detached from the recess 44. In this embodiment, as shown in FIG. 6B, each of the recesses 44 has a depth equal to or slightly larger than the thickness of the sample collection device 2. As the depth of each of the recesses 44 increases so as to be larger than the thickness of the sample collection device 2, wasted space created between the sample collection device 2 and the bottom surface of the holder 40 stacked on the holder 40 holding the sample collection device 2 in the thickness direction is larger. For this reason, as in this embodiment, the depth of each of the recesses 44 is preferably equal to or slightly larger than the thickness of the sample collection device 2.

In each of the recesses 44, a through hole 48 is formed in an area where the wide section 26 is located when the sample collection device 2 is held in the recess 44. The through hole 48 is used when the sample collection device 2 is held in the holder 40 or taken out of the holder 40 after centrifugation.

The material of the holder 40 is not particularly limited. The holder 40 may be made of the same material as the sample collection device 2.

When the holders 40 holding the sample collection devices 2 are attached to the centrifuge, these holders 40 are stacked and the empty holder 40 holding no sample collection device 2 is stacked on top of the stacked holders 40. When the holders 40 are rotated by operating the centrifuge, centrifugal force is exerted on the sample collection devices 2 in a direction from the center of rotation toward the outside of the holders 40. However, the sample collection devices 2 are not thrown out of the holders 40 in the direction of centrifugal force because the sample collection devices 2 held in the recesses 44 of each of the holders 40 are covered with a bottom surface of the other holder 40 stacked on the holder 40.

After the centrifugation, the sample collection devices 2 can be frozen for storage while being held in the holders 40. The holders 40 have a disc shape even after holding the sample collection devices 2, and therefore, the holders 40 holding the sample collection devices 2 can be stacked for storage.

Hereinbelow, an embodiment of a sample pre-processing method will be described. The sample pre-processing method is a method for collecting a sample using the sample collection device according to one embodiment of the present invention to obtain an analytical sample.

The sample pre-processing method includes the following steps (A) to (C).

(A) The sample collection device 2 is used, and the sample suction port 16 is brought into contact with a sample, for example, blood. The sample is sucked into the channel 10a and the channel 10b through the introduction channel 10c by capillary action and reaches the air hole 22.

(B) Then, the sample collection device 2 is held in the holder 40, the empty holder 40 is stacked on the holder 40, and the stacked holders 40 are attached to a centrifuge to centrifuge the sample. In this centrifugation, centrifugal force acts in a direction from the proximal end 12 toward the distal end 14 of the device main body 4. When the sample is blood, a blood cell component is collected on the distal side of the channels 10a and 10b, and plasma or serum is collected on the proximal side of the channels 10a and 10b where the extraction part 30 is provided.

(C) After the centrifugation, the extraction part 30, 30a, or 30b is cut off from the device main body 4, and is placed in a reaction container, such as a centrifuge tube, together with a pre-processing liquid to perform pre-processing.

Further, when the sample is blood and protein is an obstacle to analysis, deproteinization is also performed as pre-processing. The deproteinization can be performed by further adding an organic solvent to the reaction container after the step (C) to dissolve protein in the organic solvent and then centrifuging the reaction container. As a result of this processing, the organic solvent in which the protein is dissolved is separated from plasma or serum so that the protein is removed from the plasma or serum.

The invention claimed is:

1. A sample collection device comprising:
   a device main body that has a proximal end and a distal end and that has an opening as a sample suction port on a proximal side thereof;
   a flow channel for sample collection for sucking a sample by capillary action, the flow channel being provided in the device main body and having two channels connected to each other on a distal side of the device main body and extending from the distal side toward the proximal side of the device main body, one of the channels communicating with the sample suction port and another channel terminating before reaching the proximal end;
   an air hole that communicates with a terminal of the another channel;
   at least one extraction part that includes a portion of the one channel of the two channels and a portion of the another channel of the two channels, the portions of the one channel and the another channel being located on a distal side of the device main body than the air hole; and
   cutting grooves provided on the device main body to cut off the extraction part from a rest of the device main body.

2. The sample collection device according to claim 1, wherein
   a position of the at least one extraction part is determined so that when blood is collected as a sample and centrifuged in such a manner that centrifugal force acts in a direction from the proximal end toward the distal end of the device main body, a plasma component or a serum component is contained in the flow channel included in the at least one extraction part.

3. The sample collection device according to claim 1, wherein
   a portion of the one of the channels located between a position corresponding to the air hole and the sample suction port has a thickness smaller than that of a rest of the flow channel.

4. The sample collection device according to claim 1, wherein
   the cutting grooves comprise three or more cutting grooves provided along a direction from the distal end toward the proximal end of the device main body so that the at least one extraction part comprises two or more extraction parts.

5. The sample collection device according to claim 1, wherein
   the two channels passing through the at least one extraction part have a same thickness and are integrally formed to be separable from each other by cutting.

6. The sample collection device according to claim 1, wherein
the flow channel has a hydrophilic inner surface.

7. The sample collection device according to claim 1, wherein
the flow channel has an inner surface provided with an anticoagulant that prevents coagulation of blood.

8. The sample collection device according to claim 1, wherein
a cover that covers a distal portion of the air hole is provided on a surface of the device main body in which the air hole is provided.

9. The sample collection device according to claim 1, wherein
a liquid reservoir configured to prevent a sample from being sucked by capillary action is provided at the terminal of the another channel.

10. The sample collection device according to claim 9, wherein
the liquid reservoir has an internal capacity equal to or larger than that of a portion of the one of the channels located on a proximal side of a position corresponding to the terminal of the another channel.

11. The sample collection device according to claim 9, wherein
the liquid reservoir has a hydrophobic inner surface.

12. The sample collection device according to claim 1, wherein
a portion of the channels passing through the at least one extraction part, which passes through the cutting grooves by which the at least one extraction part is cut off from the rest of the device main body, has a thickness smaller than that of a rest of the channels.

13. The sample collection device according to claim 1, wherein
the device main body has, on a distal side of the at least one extraction part, a wide section having a width lager than that of the at least one extraction part.

14. A holder for sample collection device, comprising:
a disc-shaped supporter;
at least one recess that is provided in a surface of the supporter to fit and hold the sample collection device according to claim 1 therein in such a manner that the proximal end of the device main body faces a center of a disc of the supporter; and
an attaching part that is provided in the supporter to attach the supporter to a centrifuge.

15. The holder for sample collection device according to claim 14, wherein
the at least one recess comprises two or more recesses radially provided in the supporter.

16. The holder for sample collection device according to claim 14, wherein
the attaching part has a through hole provided at a center of the supporter, and the two or more holders for sample collection device are attached to a centrifuge via the through holes so that the holders for sample collection device are stacked.

17. A sample pre-processing method comprising following steps of:
(A) using the sample collection device according to claim 1 to suck a sample into the flow channel through the sample suction port by capillary action;
(B) then holding the sample collection device in a holder for sample collection device and centrifuging the sample collection device in such a manner that centrifugal force acts in a direction from the proximal end toward the distal end of the device main body, wherein the holder for sample collection device comprising: a disc-shaped supporter; at least one recess that is provided in a surface of the supporter to fit and hold the sample collection device according to claim 1 therein in such a manner that the proximal end of the device main body faces a center of a disc of the supporter; and an attaching part that is provided in the supporter to attach the supporter to a centrifuge; and
(C) cutting off the at least one extraction part from the device main body after the centrifugation and placing the at least one extraction part in a reaction container together with a pre-processing liquid to perform pre-processing.

18. The sample pre-processing method according to claim 17, wherein
the sample is blood, and after the step (C), an organic solvent is further added and deproteinization is performed by centrifugation.

* * * * *